US008506998B2

(12) United States Patent
Miller et al.

(10) Patent No.: US 8,506,998 B2
(45) Date of Patent: *Aug. 13, 2013

(54) PHARMACEUTICAL FORMULATION

(75) Inventors: Ronald Brown Miller, Basle (CH); Stewart Thomas Leslie, Cambridge (GB); Sandra Therese Antoinette Malkowska, Ely (GB); Derek Allan Prater, Milton (GB); Trevor John Knott, Bishops Stortford (GB); Hassan Mohammad, Haslingfield (GB)

(73) Assignee: Euro-Celtique S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 11/640,749

(22) Filed: Dec. 18, 2006

(65) Prior Publication Data

US 2007/0098795 A1 May 3, 2007

Related U.S. Application Data

(63) Continuation of application No. 10/067,451, filed on Feb. 5, 2002, now abandoned, which is a continuation of application No. 09/043,321, filed on Jul. 27, 1998, now Pat. No. 6,399,096, which is a continuation of application No. PCT/GB96/02321, filed on Sep. 20, 1996.

(30) Foreign Application Priority Data

Sep. 22, 1995 (GB) .................................. 9519363.7

(51) Int. Cl.
*A61K 9/20* (2006.01)
*A61K 9/22* (2006.01)

(52) U.S. Cl.
USPC .......................... 424/464; 424/468; 424/469

(58) Field of Classification Search
None
See application file for complete search history.

(56) References Cited

U.S. PATENT DOCUMENTS

| | | | | |
|---|---|---|---|---|
| 4,443,428 A * | 4/1984 | Oshlack et al. | ............... | 424/457 |
| 4,464,378 A | 8/1984 | Hussain | ............... | 424/260 |
| 4,609,542 A | 9/1986 | Panoz et al. | ............... | 424/19 |
| 4,797,410 A | 1/1989 | El-Fakahany | ............... | 514/356 |
| 4,806,337 A * | 2/1989 | Snipes et al. | ............... | 504/360 |
| 4,828,836 A | 5/1989 | Elger et al. | ............... | 424/419 |
| 4,834,984 A * | 5/1989 | Goldie et al. | ............... | 424/488 |
| 4,834,985 A | 5/1989 | Elger et al. | ............... | 424/488 |
| 4,844,909 A * | 7/1989 | Goldie et al. | ............... | 424/480 |
| 4,861,598 A | 8/1989 | Oshlack | ............... | 424/468 |
| 4,970,075 A | 11/1990 | Oshlack | ............... | 424/451 |
| 4,990,341 A | 2/1991 | Goldie et al. | ............... | 424/484 |
| 5,007,790 A | 4/1991 | Shell | ............... | 424/451 |
| 5,071,646 A | 12/1991 | Malkowska et al. | ............... | 424/497 |
| 5,122,384 A | 6/1992 | Paradissis et al. | ............... | 424/451 |
| 5,126,145 A * | 6/1992 | Evenstad et al. | ............... | 424/465 |
| 5,133,974 A | 7/1992 | Paradissis et al. | ............... | 424/480 |
| 5,196,203 A | 3/1993 | Boehm | ............... | 424/469 |
| 5,202,128 A | 4/1993 | Morella et al. | ............... | 424/469 |
| 5,206,030 A | 4/1993 | Wheatley et al. | ............... | 424/490 |
| 5,219,575 A | 6/1993 | Van Bommel et al. | ............... | 424/490 |
| 5,248,516 A | 9/1993 | Wheatley et al. | ............... | 427/3 |
| 5,258,436 A | 11/1993 | Wheatley et al. | ............... | 524/388 |
| 5,266,331 A | 11/1993 | Oshlack et al. | ............... | 424/464 |
| 5,273,760 A | 12/1993 | Oshlack et al. | ............... | 424/480 |
| 5,283,065 A | 2/1994 | Doyon et al. | ............... | 424/467 |
| 5,286,493 A | 2/1994 | Oshlack et al. | ............... | 424/468 |
| 5,321,012 A | 6/1994 | Mayer et al. | ............... | 514/25 |
| 5,330,766 A | 7/1994 | Morella et al. | ............... | 424/490 |
| 5,378,474 A | 1/1995 | Morella et al. | ............... | 424/469 |
| 5,384,130 A | 1/1995 | Kamada | ............... | 424/461 |
| 5,411,745 A | 5/1995 | Oshlack et al. | ............... | 424/456 |
| 5,455,046 A * | 10/1995 | Baichwal | ............... | 424/457 |
| 5,460,826 A | 10/1995 | Merrill et al. | ............... | 424/470 |
| 5,472,712 A | 12/1995 | Oshlack et al. | ............... | 424/480 |
| 5,478,577 A * | 12/1995 | Sackler et al. | ............... | 424/489 |
| 5,484,608 A * | 1/1996 | Rudnic et al. | ............... | 424/468 |
| 5,500,227 A | 3/1996 | Oshlack et al. | ............... | 424/476 |
| 5,502,058 A | 3/1996 | Mayer et al. | ............... | 514/289 |
| 5,520,931 A | 5/1996 | Persson et al. | ............... | 424/473 |
| 5,549,912 A | 8/1996 | Oshlack et al. | ............... | 424/468 |
| 5,580,578 A | 12/1996 | Oshlack et al. | ............... | 424/468 |
| 5,593,695 A | 1/1997 | Merrill et al. | ............... | 424/480 |
| 5,601,842 A | 2/1997 | Bartholomaeus | ............... | 424/464 |
| 5,614,218 A | 3/1997 | Olsson et al. | ............... | 424/456 |
| 5,629,011 A | 5/1997 | Illum | ............... | 424/434 |

(Continued)

FOREIGN PATENT DOCUMENTS

| AU | 9047732 | 7/1990 |
|---|---|---|
| AU | 9341654 | 2/1995 |

(Continued)

OTHER PUBLICATIONS

Propanolol hydrochloride Material Safety Data Sheet. Oct. 9, 2005. 6 pages.*
S. bloomfield, et al. "Analgesic Efficacy and Potency of Two Oral Controlled-Release Morphine Preparations", Clin. Pharmacol. Ther. vol. 53, No. 4, pp. 469-478, 1993.
Advertisement: MS Conlin 1986, 1987 The Purdue Fredrick Company.
R. Kaiko and T. Hunt, "Comparision of the Pharmacokinetic Profiles of Two Oral Controlled-Release Morphine Formulations in Healthy Young Adults", Clinical Therapeutics. vol. 13, No. 4, pp. 484-488, 1991.
R. West et al., World Congress on Pain Abstracts 997-1001, Aug. 26, 1993.

(Continued)

*Primary Examiner* — Lakshmi Channavajjala
(74) *Attorney, Agent, or Firm* — Davidson, Davidson & Kappel, LLC

(57) ABSTRACT

A solid, oral controlled release pharmaceutical dosage form has a water-soluble active ingredient dispersed in a matrix and releases the active ingredient at such a rate upon administration that the median tmax is 2.5 to 6 hours and the ratio of mean Cmax to mean plasma level of the active ingredient at 24 hours is in the range of 1.5 to 3.5.

34 Claims, No Drawings

(56) References Cited

U.S. PATENT DOCUMENTS

| | | | |
|---|---|---|---|
| 5,637,320 A | 6/1997 | Bourke et al. | 424/489 |
| 5,654,005 A | 8/1997 | Chen et al. | 424/480 |
| 5,656,295 A | 8/1997 | Oshlack et al. | 424/468 |
| 5,667,805 A | 9/1997 | Merrill et al. | 424/473 |
| 5,670,172 A | 9/1997 | Buxton et al. | 424/495 |
| 5,672,360 A * | 9/1997 | Sackler et al. | 424/490 |
| 5,681,585 A | 10/1997 | Oshlack et al. | 424/494 |
| 5,709,883 A | 1/1998 | Drizen et al. | 424/488 |
| 5,849,240 A | 12/1998 | Miller et al. | 264/460 |
| 5,879,705 A | 3/1999 | Heafield et al. | 424/464 |
| 5,891,471 A | 4/1999 | Miller et al. | 424/468 |
| 5,965,163 A | 10/1999 | Miller et al. | 424/468 |
| 6,103,261 A * | 8/2000 | Chasin et al. | 424/459 |
| 6,143,328 A | 11/2000 | Heafield et al. | 424/489 |
| 6,399,096 B1 | 6/2002 | Miller et al. | 424/464 |

FOREIGN PATENT DOCUMENTS

| | | |
|---|---|---|
| CA | 2131350 | 3/1995 |
| EP | 0271193 | 6/1988 |
| EP | 0548448 | 6/1990 |
| EP | 0377517 | 7/1990 |
| EP | 0377518 | 7/1990 |
| EP | 0533297 | 3/1993 |
| EP | 0553392 | 8/1993 |
| EP | 0609961 | 8/1994 |
| EP | 0636370 | 2/1995 |
| WO | 8909066 | 10/1989 |
| WO | 9201446 | 2/1992 |
| WO | 9206679 | 4/1992 |
| WO | 9208459 | 5/1992 |
| WO | 9310765 | 6/1993 |
| WO | 9403160 | 2/1994 |
| WO | 9403161 | 2/1994 |
| WO | 9405262 | 3/1994 |
| WO | 9422431 | 10/1994 |
| WO | 9614058 | 5/1996 |

OTHER PUBLICATIONS

Thomsen, L. Juul, Prolonged Release Matrix Pellets Prepared by Melt Pelletization. Part IV: Drug Content, Drug Particle Size, and Binder Composition, Pharmaceutical Technology Europa, pp. 19-24 (Oct. 1994).

Gourlay et al., Proceeding of the 7th World Congress on Pain: A Comparison of Kapanol ( A New Sustained Release Morphine Formulation), MST Conlinus, and Morphine Solution in Cancer Patients: Pharmokinetic Aspects of Morphine and Morphine Metabolites, Progress in Pain Research and Management vol. 2 pp. 631-643 (1994).

R.F. Kaiko, The Pre and Postoperative Use of Controlled Release Morphine (MS Contin Tablets): A review of Published Literature , Medical Department , The Purdue Fredrick Company, Royal Society of Medical Services, International Congress, Symposium Services, No. 149, pp. 147-160 (1989).

J. Lapin et al., "Cancer Pain Management with a Controlled Release Oral Morphine Preparation", *Journal of Pain and Symptom Management*, V4 (3), pp. 146-151, 1989.

J. Lapin et al., "Guidelines for Use of Controlled Release Oral Morphine in Cancer Pain Management", *Cancer Nursing*, V12 (4), pp. 202-208, 1989.

R.F. Kaiko, "Clinical Protocaol and Role of Controlled Release Morphine in the Surgical Patient", *Anesthesiology and Pain Management* pp. 193-212, 1991.

European Journal of Cancer, Once a Day (i.e. 24 Hourly) Kapanol™, A new sustained Release Morphine Formulation, In the Treatment of Cancer Pain: Pharmacokinetic Aspects; Part A General Topics 1995: 31 (S5) Suppl: S187 Abs 897 European Conference on Clinical Oncology and Cancer Nursing, Paris, Oct. 29-Nov. 2, 1995.

European Journal of Cancer, Kadlan™/ Kapanol™—A once Daily Morphine Formulation ; Part A General Topics 1995; 31 (S5) Suppl: S182 Abs 873 European Conference on Clinical Oncology and Cancer Nursing, Parts, Oct. 29-Nov. 2, 1995.

Maccarrone C. et al.; Single Dose Pharmacokinetics of Kapanol™, a New Oral Sustained-Release Morphine Formulation; Clinical Drug Investigation 1994:7 (5) 262-274.

West R.J. Maccarrone C. Single dose pharmacokinetics of new oral sustained release morphine formulation, Kapanol™ capsules. (Abstract 997) International Association for the Study of Pain, $7^{th}$ World Congress on Pain. Paris, Aug. 22-27, 1993 (Data on file, Glaxo Australia, F.H. Faulding).

Gourlay GK, Plummer JL, Cherry DA, et al. A comparison of Kapanol™ (A new sustained release morphine formulation), MST Continus® and morphine solution in cancer patients: pharmacokinetic aspects. (Abstract 998) International Association for the Study of Pain, $7^{th}$ World Congress on Pain. Paris, Aug. 22-27, 1993 (Data on file, Glaxo Australia, F.H. Faulding).

Cherry DA, Gourley GK, Plummer JL, et al. A comparison of Kapanol™ (a new sustained release morphine formulation), MST Continus® and morphine solution in cancer patients: morphine metabolite profiles and renal function. (Abstract 999) International Association for the Study of Pain, $7^{th}$ World Congress on Pain, Paris, Aug. 22-27, 1993 (Data on file, Glaxo Australia, F.H. Faulding).

Plummer JL, Cherry DA, Gouday GK, et al. A comparison of Kapanol™ (a new sustained release morphine formulation) MST Continus® and morphine solution in cancer patients: pharmacodynamic aspects. (Abstract 1000) International Association for the Study of Pain, $7^{th}$ World Congress on Pain, Paris, Aug. 22-27, 1993 (Data on file, Glaxo Australia, F.H. Faulding).

Toner G, Cramond T, Bishop, et al. Randomized double blind, phase III crossover study of a new sustained-release oral morphine formulation, Kapanol™ capsules, (Abstract 1001) International Association for the Study of Pain, $7^{th}$ World Congress on Pain, Paris, Aug. 22-27, 1993 (Data on file, Glaxo Australia, F.H. Faulding).

European Journal of Cancer; Once a Day (i.e. 24 Hourly) Kapanol™, A New Sustained Release Morphine Formulation, in the Treatment of Cancer Pain: Morphine Metabolite Profiles; Part A General Topics 1995; 31 (S5) Suppl:S184 Abs 884, European Conference on Clinical Oncology and Cancer Nursing, Paris, Oct. 29-Nov. 2, 1995.

Thomsen, L. Juul, "Utilizing Melt Pelletization Technique for the Preparation of Prolonged Release Products", *Pelletization*, (material elaborated by assistant professor Lars Juul Thomsen, Department of Pharmaceutics, Royal Danish School of Pharmacy for the DIE course "Pelletization Technology", Nov. 1992, 106 pages, plus 3 appendices.

Annuzlata et al., "Effect of polyethylene glycol on the liquid-liquid phase transition in aqueous protein solutions", PNAS, vol. 99, No. 22 (Oct. 29, 2002) pp. 14165-14170.

\* cited by examiner

PHARMACEUTICAL FORMULATION

This application is a continuation of U.S. application Ser. No. 10/067,451, filed Feb. 5, 2002, which is a continuation of U.S. application Ser. No. 09/043,321, filed Jul. 27, 1998, now U.S. Pat. No. 6,399,096, which is a national phase filing of International PCT Application No. PCT/GB96/02321, filed Sep. 20, 1996, published as WO 97/10826, which claims priority to Great Brittan Application Serial No. GB 9519363.7, filed Sep. 22, 1995, the disclosures of which are hereby incorporated by reference in their entireties.

This invention relates to a solid, oral, controlled release pharmaceutical dosage form.

The literature is replete with examples of controlled release pharmaceutical preparations for oral usage.

PCT/SE93/00642 describes an oral morphine preparation having essentially complete bioavailability and, for the major part of the dissolution, an essentially zero order and essentially pH independent release of morphine for a period of at least 8 hours. In the form of a tablet having a core containing morphine sulphate and a buffering agent, the tablet core being coated with a diffusion membrane comprising a terpolymer of vinyl chloride, vinylacetate and vinylalcohol.

EP 0377518 describes a sustained release pellet composition containing a core element including at least one active ingredient of high solubility, and a core coating for the core element which is partly soluble at a highly acidic pH to provide a slow rate of release of active ingredient and wherein the active ingredient is available for absorption at a relatively constant faster rate in the intestines over an extended period of time such that blood levels are maintained within the therapeutic range over an extended period of time. A typical embodiment in this patent publication is a morphine sulphate containing preparation suitable for twice a day dosing obtained by a process which comprises coating core seeds with the active ingredient and then coating the resulting core seeds with a controlled release coating material containing ethyl cellulose, an acrylic co-polymer, a plasticiser and a detackifying agent using a solution of the aforesaid substances in an organic solvent.

PCT/SE94/00264 Describes controlled release preparations containing a salt of morphine, comprising a number of core seeds coated with a barrier membrane. In the Example a conventional granulation is carried out with morphine hydrochloride, lactose and microcrystalline cellulose. The resulting morphine hydrochloride cores are then coated with a controlled release membrane containing hydroxypropyl methyl cellulose, ethyl cellulose and plasticisers using a solution of these substances in a mixed solvent of ethanol and methyl isobutyl ketone.

PCT/SE93/0025 describes a process for manufacturing sustained release pellets comprising pelletizing a mixture of a drug in finely divided form and a binder consisting of one or more water-insoluble wax-like binder substances with a melting point above 40° C., the pelletization being performed by mechanically working the mixture in a high shear mixer under the input of a sufficient amount of energy for the binder to melt and pelletization to take place. In a typical example in this patent publication paracetamol is pelletized using glycerol. Monostearate and optionally a lipophilic binder substance such as stearyl alcohol, triglyceride DS, Beeswax or microcrystalline wax, together with calcium hydrogen phosphate as a filler.

EP 0636370 describes a sustained release pharmaceutical formulation containing morphine which is suitable for administration on a once daily basis. The dosage form is typically in the form of multiparticulates obtained by mechanically working in a high shear mixer a pharmaceutically acceptable morphine salt and a hydrophobic fusible carrier or diluent having a melting point from 35° C. to 150° C. and optionally a release control component comprising a water-soluble fusible material or a particulate, soluble or insoluble organic or inorganic material, at a speed and energy input which allows the carrier or diluent to melt or soften whereby it forms agglomerates. Breaking down the agglomerates to give controlled release particles and optionally continuing mechanically working optionally with the addition of a low percentage of the carrier or diluent.

Embodiments are described in EP 0636370 in which the mean Cmax obtained in a group of five health volunteers when dosed at 60 mg of morphine sulphate is approximately 8 ng/ml and the $W_{50}$ value for morphine is approximately 8.6 hours.

The mean plasma curve includes a relatively high peak of about 10 ng/ml at about 3 hours after dosing which tails off rapidly to reach a fairly stable, but declining level about 12 hours after dosing, with the ratio of mean Cmax to the mean plasma level at 24 hours of about 4.5.

According to the present invention there is provided a solid, oral, controlled release pharmaceutical dosage form which comprises a pharmaceutically active ingredient having a solubility in water of greater than 1 gm in 250 ml water at 25° C. dispersed in a controlled release matrix, wherein the dosage form when tested by the Ph. Eur. Basket method at 100 rpm 900 ml aqueous buffer (pH 6.5) containing 0.05% w/w. Polysorbate 80 at 37° C. has an essentially zero order rate of release of the pharmaceutically active ingredient over a period of 8 hours. The amount of pharmaceutically active ingredient released over eight hours being in the range of 15% to 45% by weight, and when tested in a group of at least five healthy humans the median tmax, based on blood sampling at half hourly intervals, is in the range of from 2.5 to 6 hours, and the ratio of mean Cmax to the mean plasma level at 24 hours is in the range of 1.5 to 3.5.

Polysorbate 80 is described in entry 7559 at page 1207 in Merck Index, Eleventh Edition 1989 published by Merck & Co. Inc. It is an oleate ester of sorbitol and its anhydrides copolymerised with approximately 200 moles of ethylene oxide for each mole of sorbitol and sorbitol anhydrides.

A preferred dosage form in accordance with the invention has a median tmax in the range from 2.5 to 3.5 hours.

In a preferred embodiment the dosage form according to the present invention has a mean $W_{50}$ in the range from 15 to 35 hours, more preferably 20 to 30 hours when tested in vivo as set forth above.

In preferred embodiments the matrix comprises an hydrophobic, fusible material having a melting point of greater than 40° C. and may also include a wicking agent which may be a hydrophilic, organic, polymeric, fusible substance or a particulate soluble or insoluble inorganic material.

In embodiments of the process of the invention described below it is believed the resulting matrix comprises an inner region which is a mixture comprising an hydrophobic, fusible material and active ingredient and preferably wicking agent surrounded by a contiguous, outer, mantle region comprising an hydrophobic, fusible material have a reduced concentration of, or being substantially free from, said pharmaceutically active ingredient and wicking agent, though the invention is not limited to this theory.

The pharmaceutically active ingredient is preferably present in an amount suitable for twice or once a day dosing. The preferred active ingredient is morphine or a pharmaceutically acceptable salt of morphine, preferably morphine sulphate or morphine hydrochloride and is preferably present in an amount suitable for once a day dosing. The dosage forms may preferably contain 30 to 400 mg of morphine as pharmaceutically acceptable salt.

The dosage form of the invention is conveniently in the form of a tablet or a capsule containing multiparticulates.

Although morphine and pharmaceutically acceptable morphine salts have been mentioned above as preferred active ingredients, other suitable water soluble active ingredients include hydromorphone hydrochloride, diamorphine hydrochloride, tramadol hydrochloride and dihydrocodeine tartrate.

Preferably the weight ratio of hydrophobic, fusible material to wicking agent in the matrix or inner region thereof is in the range from 8:1 to 16:1 preferably 8:1 to 12:1.

Suitably the weight ratio of hydrophobic, fusible material in the said mixture to hydrophobic, fusible material in the mantle region is in the range of from 3:1 to 12:1.

Suitable hydrophobic, fusible materials are natural or synthetic waxes, oils, fatty acid glycerides or other esters for example hydrogenated vegetable oil or castor oil and suitable hydrophilic, organic, fusible wicking agents include polyethylene glycols (PEGs) of various molecular weights e.g. 1,000 to 20,000 preferably 4,000 to 10,000 and suitable particulate inorganic wicking agents include dicalcium phosphate and lactose. It is preferred to use an hydrophilic fusible, organic polymeric as wicking agent.

The dosage forms of the present invention have a significantly lower Cmax and greater $W_{50}$ than dosage forms made according to the method described in EP 636370 whilst surprisingly retaining an advantageously short median tmax of 2.5 to 6 hours.

Dosage forms of the present invention can be prepared by a process comprising:—
(a) mechanically working in a high shear mixer a mixture of hydrophobic. Fusible binder and a minor amount of an organic, fusible, polymeric material which in the finished dosage form is capable of functioning as a wicking agent at a speed and temperature at which the binder melts or softens and the mixture forms agglomerates;
(b) extruding the agglomerates whereby the extrudate is obtained as extruded pieces or an elongate extrudate is formed into pieces;
(c) continuing mechanically working the pieces in a high shear mixer suitably until particles of reproducible in vitro release rate when tested according to the in vitro method set forth above have been achieved; and
(d) continuing mechanically working with additional binder material at a temperature and speed at which the additional binder melts or softens and binds with the particles.

A preferred process uses identical hydrophobic, fusible material in stage (d) as in stage (a).

Preferably in stage (a) the weight ratio of hydrophobic, fusible material to wicking agent, preferably hydrophobic, organic, polymeric wicking agent used is in the range from 8:1 to 16:1 preferably 8:1 to 12:1.

Preferably the weight ratio of hydrophobic, fusible material used in stage (a) to hydrophobic, fusible material use in stage (d) is in the range from 3:1 to 12:1 preferably 3:1 to 7:1.

The resulting multiparticulates may be sieved or otherwise size selected and filled into capsules e.g. hard gelatine capsules, or may be compressed into tablets. Usually the particles are of a size 0.5 mm to 3.0 mm and a spherical or spheroidal.

The higher shear mixer may be one conventionally used in the pharmaceutical formulation art and we have found satisfactory results can be achieved using a Collette Gral 75 or equivalent mixer.

Generally in stage (a) the mixture is processed until a bed temperature above 40° C. is achieved and the mixture softens but does not melt and the resulting mixture acquires a cohesive granular texture, with particles ranges from 0.5 to 3.0 mm to fine powder in case of non-aggregated material. The mixture may be processed until it has the appearance of agglomerates which, upon cooling below 40° C. have structural integrity and resistance to crushing between the fingers. At this stage the agglomerates are of an irregular size, shape and appearance. The resulting mass is then extruded.

Extrusion may be carried out by passing the agglomerates through a conventional extruder e.g. a Caleva extruder. An extruder may be used fitted with gears with suitably sized holes to provide pieces of desired size.

Usually the extrusion is though orifices having a diameter of about 0.25 mm to 1.5 mm eg 0.5 mm or 1.0 mm. The length of the extrudate pieces may be eg 0.5 to 1.5 cm eg 1.0 cm.

The preparation avoids the complicated forms of prior art preparations in that it does not require the use of controlled release coatings or buffers, whilst at the same time enabling dosing at only twice preferably once a day and without large fluctuations in blood plasma levels during the dosing intervals.

EXAMPLE 1

The bowl of a Collette Gral 10 was preheated to a jacket temperature of 61° C. and allowed to stabilise. 540.5 g of morphine sulphate. 36 g of polyethylene glycol 6000 and 343.2 g of hydrogenated vegetable oil were placed in the pre-heated jacketed bowl and left to warm with no mixing for about 4 minutes.

The machine was then run for about 20 to 25 minutes with mixer and chopper blades running at 425 rpm and setting 1 respectively.

The resulting granules/agglomerates were then immediately removed and passed through a Caleva extruder fitted with 1 mm hole gears.

The extruded pieces were placed in the bowl of the Collette Gral 10 which had been preheated to a jacket temperature of 61° C. and left with no mixing for 4 minutes. Processing was then carried out as follows:—
(a) for 4 minutes at mixer speed 100 rpm and chopper speed setting 1;
(b) for 4 minutes at mixer speed 200 rpm, chopper setting 1 and jacket temperature 58° C.; and
(c) for 9 minutes at mixer speed 400 rpm, chopper setting 1 and jacket temperature 55° C.
(d) 73 g of hydrogenated vegetable oil were then added and processing was continued under the same conditions for a further minute.

The resulting multiparticulates were immediately passed through a sieve (0.5 to 2.0 mm) and the 0.5-2.0 mm fraction retained.

The retained multiparticulates were mixed with minor amounts of talc and magnesium stearate and encapsulated in hard gelatine capsules so that each capsule contained the following constituents.

|  | mg |
|---|---|
| Morphine Sulphate BP | 60.00 |
| Hydrogenated vegetable oil NF | 46.10 |
| Polyethylene glycol 6000 Ph Eur | 4.00 |

-continued

|  | mg |
|---|---|
| Talc Ph Eur | 0.55 |
| Magnesium Stearate Ph Eur | 0.33 |

EXAMPLE 2

Example 1 was repeated using 526 g of morphine sulphate, 35 g of polyethylene glycol 6000, and 334 g hydrogenated vegetable oil in the initial processing and subsequently adding 88 g of hydrogenated vegetable oil in stage (d). Capsules were obtained containing multiparticulates having the following constituents:—

|  | mg/capsule |
|---|---|
| Morphine sulphate BP | 60.00 |
| Hydrogenated vegetable oil NF | 48.10 |
| Polyethylene glycol 600 Ph. Eur. | 4.0 |
| Talc Ph. Eur. | 0.56 |
| Magnesium stearate Ph. Eur | 0.33 |

REFERENCE EXAMPLE 1

The multiparticulates obtained in Examples 1 and 2 were tested using the Ph. Eur Basket 100 rpm in 900 ml aqueous buffer (pH 6.5) containing 0.05% w/v Polysorbate 80 at 37° C. and the release rates of morphine are shown in Table 1.

|  | % Morphine released (mean) | |
|---|---|---|
| Hour | Example 1 | Example 2 |
| 1 | 4.7 | 2.7 |
| 2 | 8.6 | 5.4 |
| 3 | 12.6 | 8.1 |
| 4 | 16.3 | 11.0 |
| 5 | 20.4 | 13.8 |
| 6 | 24.3 | 16.8 |
| 8 | 32.2 | 22.9 |
| 10 | 39.7 | 29.3 |
| 14 | 53.4 | 41.1 |
| 24 | 76.6 | 62.7 |

REFERENCE EXAMPLE 2

The capsules obtained in Examples 1 and 2 and, by way of comparison, capsules obtained according to EP-A-636370 were tested in a single dose study in five healthy blood samples were taken every half hour.

The results are as shown in the following tables 2, 3 and 4.

TABLE 2

CAPSULE ACCORDING TO EP-A 636370 CONTAINING 60 MG MORPHINE SULPHATE

| Vol | Cmax (ng/ml) | tmax (h) | W50 (h) | C24 (ng/ml) | Cmax/C24 |
|---|---|---|---|---|---|
| 1 | 9.42 | 5 | 7.25 | 2.63 | 3.58 |
| 2 | 1.50 | 4 | 5.47 | 1.59 | 7.23 |
| 3 | — | — | — | — | — |
| 4 | 11.72 | 3 | 5.19 | 2.45 | 4.78 |

TABLE 2-continued

CAPSULE ACCORDING TO EP-A 636370 CONTAINING 60 MG MORPHINE SULPHATE

| Vol | Cmax (ng/ml) | tmax (h) | W50 (h) | C24 (ng/ml) | Cmax/C24 |
|---|---|---|---|---|---|
| 5 | 7.12 | 3 | 15.68 | 2.77 | 2.57 |
| 6 | 11.33 | 3 | 4.01 | 2.38 | 4.76 |
| Mean | 10.22 | | 7.52 | 2.36 | 4.58 |
| sd | 1.96 | | 4.71 | 0.46 | 1.74 |
| Median | | 3 | | | |
| Range | | 3–5 | | | |

TABLE 3

CAPSULE ACCORDING TO EXAMPLE 1

| Vol | Cmax (ng/ml) | tmax (H) | W50 (h) | C24 (ng/ml) | Cmax/C24 |
|---|---|---|---|---|---|
| 1 | 5.32 | 3 | 43.30 | 3.12 | 1.71 |
| 2 | 4.55 | 5 | 34.88 | 2.33 | 1.95 |
| 3 | 3.87 | 3 | 52.38 | 1.84 | 2.10 |
| 4 | 8.37 | 3 | 19.23 | 3.58 | 2.34 |
| 5 | 8.24 | 3 | 5.37 | 2.89 | 2.85 |
| 6 | 5.90 | 3 | 12.98 | 2.90 | 2.03 |
| Mean | 6.04 | | 28.02 | 2.78 | 2.16 |
| sd | 1.88 | | 18.39 | 0.61 | 0.39 |
| Median | | 3 | | | |
| Range | | 3–5 | | | |

TABLE 4

CAPSULE ACCORDING TO EXAMPLE 2

| Vol | Cmax (ng/ml) | tmax (H) | W50 (h) | C24 (ng/ml) | Cmax/C24 |
|---|---|---|---|---|---|
| 1 | 4.72 | 13 | 33.45 | 2.98 | 1.58 |
| 2 | 3.93 | 3 | 36.84 | 2.50 | 1.57 |
| 3 | — | — | — | — | — |
| 4 | 6.91 | 3 | 20.63 | 3.41 | 2.03 |
| 5 | 5.90 | 3 | 24.93 | 3.08 | 1.92 |
| 6 | 6.31 | 3 | 13.15 | 2.60 | 2.43 |
| Mean | 5.55 | | 25.80 | 2.91 | 1.91 |
| sd | 1.21 | | 9.59 | 0.37 | 0.36 |
| Median | | 3 | | | |
| Range | | 3–13 | | | |

The invention claimed is:

1. A solid, oral, controlled release pharmaceutical dosage form, comprising
one pharmaceutically active ingredient consisting of a pharmaceutically acceptable salt, of morphine, diamorphone, tramadol and dihydrocodeine, the pharmaceutically active ingredient having a solubility in water of greater than 1 gm in 250 ml water at 25° C., dispersed in a matrix of a controlled release material consisting of a hydrophobic fusible material having a melting point of greater than 40° C., and a hydrophilic, organic, polymeric fusible wicking agent,
wherein the weight ratio of the hydrophobic fusible material to the hydrophilic, organic polymeric wicking agent in said matrix is in the range from 8:1 to 16:1, and
the dosage form provides, as tested by the Ph. Eur. Basket method at 100 rpm 900 ml aqueous buffer (pH 6.5) containing 0.05% w/w Polysorbate 80 at 37° C., an essentially zero order rate of release of the pharmaceutically active ingredient over a period of 8 hours, an amount of pharmaceutically active ingredient released over eight hours in the range of 15% to 45%, and, when tested in a group of at least five healthy humans, a median tmax, based on blood sampling at half hourly intervals, in the range of from 2.5 to 6 hours,
a ratio of mean Cmax to the mean plasma level at 24 hours in the range of 1.5 to 3.5, and a $W_{50}$ in the range from 15 to 35 hours, and
said pharmaceutically active ingredient is the only pharmaceutically active ingredient in the dosage form.

2. A pharmaceutical dosage form according to claim 1, wherein the median tmax is in the range from 2.5 to 3.5 hours.

3. A pharmaceutical dosage form according to claim 1, in which the pharmaceutically active ingredient is a pharmaceutically acceptable salt of morphine.

4. A pharmaceutical dosage form according to claim 1, which is suitable for once a day dosing.

5. A pharmaceutical dosage form according to claim 1, in the form of a tablet or a capsule containing multiparticulates.

6. A solid, oral, controlled release pharmaceutical dosage form which comprises
one pharmaceutically active ingredient consisting of a pharmaceutically acceptable salt, of morphine, diamorphone, tramadol and dihydrocodeine,
the pharmaceutically active ingredient having a solubility in water of greater than 1 gm in 250 ml water at 25° C., dispersed in a matrix of a controlled release material consisting of a hydrophobic fusible material having a melting point of greater than 40° C., and a hydrophilic, organic polymeric fusible wicking agent,
wherein the weight ratio of the hydrophobic fusible material to the hydrophilic, organic polymeric wicking agent in said matrix is in the range from 8:1 to 16:1,
said one pharmaceutically active ingredient is the only pharmaceutically active ingredient in the dosage form,
the dosage form provides a dissolution rate in-vitro when measured by the Ph. Eur. Basket method at 100 rpm 900 ml aqueous buffer (pH 6.5) containing 0.05% w/w Polysorbate 80 at 37° C. such that an amount of the pharmaceutically active ingredient released from the dosage over eight hours is in the range of 15% to 45% (by weight), and is being obtainable by a process comprising:
(a) mechanically working in a high shear mixer a mixture of a hydrophobic fusible binder and an amount of an organic, fusible, polymeric material which in the finished dosage form is capable of functioning as a wicking agent at a speed and temperature at which the binder melts or softens and the mixture forms agglomerates;
(b) extruding the agglomerates whereby the extrudate is obtained as extruded pieces or an elongate extrudate is formed into pieces;
(c) continuing mechanically working the pieces in a high shear mixer; and
(d) continuing mechanically working with additional binder material at a temperature and speed at which the additional binder melts or softens.

7. A pharmaceutical dosage form according to claim 1, which has a $W_{50}$ in the range from about 20 to about 30 hours when tested in vivo as set forth in claim 1.

8. A pharmaceutical dosage form according to claim 1, in which the pharmaceutically active ingredient is morphine sulfate or morphine hydrochloride.

9. A pharmaceutical dosage form according to claim 6, which provides a median $t_{max}$ in the range from about 2.5 to about 3.5 hours.

10. A pharmaceutical dosage form according to claim 6 which provides a $W_{50}$ in a range from about 15 to about 35 hours.

11. A pharmaceutical dosage form according to claim 6 which provides a $W_{50}$ in a range from about 20 to about 30 hours.

12. A pharmaceutical dosage form according to claim 6 wherein the pharmaceutically active ingredient is a pharmaceutically acceptable salt of morphine.

13. A pharmaceutical dosage form according to claim 6, wherein the pharmaceutically active ingredient is morphine sulfate or morphine hydrochloride.

14. A pharmaceutical dosage form according to claim 1, wherein the pharmaceutically active ingredient is selected from the group consisting of hydromorphone hydrochloride, diamorphine hydrochloride, tramadol hydrochloride and dihydrocodeine tartrate.

15. A pharmaceutical dosage form according to claim 6, wherein the pharmaceutically active ingredient is selected from the group consisting of hydromorphone hydrochloride, diamorphine hydrochloride, tramadol hydrochloride and dihydrocodeine tartrate.

16. A pharmaceutical dosage form according to claim 6, which is suitable for once a day dosing.

17. A pharmaceutical dosage form according to claim 6, in the form of a tablet or capsule containing multiparticulates.

18. A pharmaceutical dosage form according to claim 5, in the form of a tablet.

19. A pharmaceutical dosage form according to claim 1, wherein the hydrophobic, fusible material is selected from the group consisting of natural or synthetic waxes, oils, fatty acid glycerides and esters.

20. A pharmaceutical dosage form according to claim 1, wherein the hydrophilic, organic, fusible wicking agent is polyethylene glycol.

21. A pharmaceutical dosage form according to claim 20, wherein the polyethylene glycol has a molecular weight of 1000 to 20000.

22. A pharmaceutical dosage form according to claim 6, wherein the hydrophobic, fusible material is selected from the group consisting of natural or synthetic waxes, oils, fatty acid glycerides and esters.

23. A pharmaceutical dosage form according to claim 6, wherein the hydrophilic, organic, fusible wicking agent is polyethylene glycol.

24. A pharmaceutical dosage form according to claim 23, wherein the polyethylene glycol has a molecular weight of 4000 to 20000.

25. A pharmaceutical dosage form according to claim 1, wherein the hydrophobic, fusible material is a hydrogenated vegetable oil.

26. A pharmaceutical dosage form according to claim 6, wherein the hydrophobic, fusible material is a hydrogenated vegetable oil.

27. A pharmaceutical dosage form according to claim 6, wherein the dosage form provides, when tested in a group of at least five healthy humans, a median tmax, based on blood sampling at half hourly intervals, in the range of from 2.5 to 6 hours, the ratio of mean Cmax to the mean plasma level at 24 hours in the range of 1.5 to 3.5, and a $W_{50}$ in the range from 15 to 35 hours.

28. A pharmaceutical dosage form according to claim 6, wherein the dosage form provides, as tested by the Ph. Eur. Basket method at 100 rpm 900 ml aqueous buffer (pH 6.5) containing 0.05% w/w Polysorbate 80 at 37° C., an essentially zero order rate of release of the pharmaceutically active ingredient over a period of 8 hours.

29. A pharmaceutical dosage form according to claim 1, wherein the active ingredient and the wicking agent are in an inner region of the matrix, the hydrophobic, fusible material is in the inner region and in an outer mantle region of the matrix, and the outer region of the matrix is substantially free from the active ingredient.

30. A pharmaceutical dosage form according to claim 1, wherein the active ingredient and the wicking agent are in an inner region of the matrix, the hydrophobic, fusible material is in the inner region and in an outer mantle region of the matrix, and the outer mantle region of the matrix is substantially free from the active ingredient and the wicking agent.

31. A pharmaceutical dosage form according to claim 30, wherein the ratio of the hydrophobic fusible material to the wicking agent in the inner region is in the range from 8:1 to 16:1.

32. A pharmaceutical dosage form according to claim 6, wherein the active ingredient and the wicking agent are in an inner region of the matrix, the hydrophobic, fusible material is in the inner region and in an outer mantle region of the matrix, and the outer region of the matrix is substantially free from the active ingredient.

33. A pharmaceutical dosage form according to claim 6, wherein the active ingredient, and the wicking agent are in an inner region of the matrix, the hydrophobic, fusible material is in the inner region and in an outer mantle region of the matrix, and the outer mantle region of the matrix is substantially free from the active ingredient and the wicking agent.

34. A pharmaceutical dosage form according to claim 33, wherein the ratio of the hydrophobic fusible material to the wicking agent in the inner region is in the range from 8:1 to 16:1.

* * * * *